United States Patent [19]

Adibi et al.

[11] Patent Number: 5,034,377

[45] Date of Patent: Jul. 23, 1991

[54] AQUEOUS NUTRIENT COMPOSITIONS COMPRISING OLIGOPEPTIDES

[75] Inventors: Siamak A. Adibi, Pittsburgh, Pa.; Maria Brandl, Schwabach, Fed. Rep. of Germany; Werner Fekl, Rottenbach, Fed. Rep. of Germany; Klaus Langer, Erlangen, Fed. Rep. of Germany

[73] Assignee: Montefiore Hospital Association of Western Pennsylvania, Pa.

[21] Appl. No.: 436,972

[22] Filed: Nov. 16, 1989

Related U.S. Application Data

[63] Continuation of Ser. No. 795,193, Nov. 5, 1985, abandoned, which is a continuation-in-part of Ser. No. 673,010, Nov. 19, 1984, abandoned.

[51] Int. Cl.$^5$ .................... A61K 37/02; A61K 37/18; A23J 1/00
[52] U.S. Cl. ...................................... 514/18; 514/19; 426/656; 426/810
[58] Field of Search .................... 514/18, 19; 426/656, 426/810

[56] References Cited

U.S. PATENT DOCUMENTS 4,340,592  7/1982  Adibi ...................................... 514/19

FOREIGN PATENT DOCUMENTS 3206784  9/1983  Fed. Rep. of Germany .

OTHER PUBLICATIONS

Adibi et al., *Gastroenterology*, vol. 86, No. 6, 1562–1569 (1984).
Albers et al., 6th *Congress of the European Society of Parenteral and Enteral Nutrition*, 1–3 Oct. 1984, Milan, Italy.
Richards et al., *Chem. Abst.*, 101, 118 (1984. abst no 123621g.
Meyer-Glauner et al., *Chem. Abst.*, 97, 379 (1982). abst no. 141561y.
Furst et al., Peptides in Parenteral Nutrition Oct. 1984, 6th Congress Eur. Soc. Par. Ent. Nutr.
Adibi et al., Efficacy of Synthetic Dipeptide Mixture . . ., 1984, Gastroenterology 86, 1566–1567.
Heller, Clinical and Experimental Studies . . . Nutrition, 1968, Scand. J. Parenteral Nutrition, pp. 7–16.
Berg, Recommendations for Parenteral Nutrition 1964, Int. Soc. Parenteral Nutrition, pp. 2, 4, 36, 37.
Heller, Fortschritte Der Parenteral Ernahrung, 1967, Int. Soc. Parenteral Nutrition, p. 32 (Abstract).
Fischer, Total Parenteral Nutrition (No Date Shown), Chapter 2, p. 5.
Christensen et al., The Conjugated, Non-Protein Amino Acids of Plasma, 1947, J. Clin. Invest. 26:849–852.
Frey et al., The Importance of Amino Acids in Parenteral Alimentation 1975, Proc. Int. Sym. Int. Therapy, pp. 40–46.
Adibi et al., Metabolism of Intravenously Administerd Peptides, 1977, Clin. Sci. Mol. Med., 52: 193–204.
Adibi et al. Effect of Naphrectomy . . . Dipeptide in Rat 1977 Clin. Sci. Mol. Med. 52:205–213.
Adibi et al., Enrichment of Glycine Pool . . . 1982, Am. J. Physiol. 243; E 413–417.

*Primary Examiner*—Ronald W. Griffin
*Attorney, Agent, or Firm*—Harry B. Keck

[57] ABSTRACT

A nutrient composition includes at least two oligopeptides of amino acids having in the N-terminal position of at least one oligopeptide a residue of glycine and having in the N-terminal position of at least one oligopeptide a residue of L-alanine, L-lysine or L-arginine. The aqueous compositions may also contain free amino acids and may contain other nutrient substances such as fats, oligosaccharides, minerals, trace elements, vitamins and free amino acids. The compositions are intended for oral or parenteral use with mammals. Compositions having dipeptide concentrations higher than prior art compositions are disclosed. Compositions containing elevated concentrations of total protein greater than heretofor proposed employ both the described oligopeptides and also free amino acids.

14 Claims, No Drawings

AQUEOUS NUTRIENT COMPOSITIONS COMPRISING OLIGOPEPTIDES

CROSS REFERENCE TO RELATED APPLICATIONS

This application is a continuation of co-pending application Ser. No. 795,193 (now abandoned) filed Nov. 5, 1985 as a Continuation-in-Part of copending application Ser. No. 673,010 filed Nov. 19, 1984, now abandoned.

BACKGROUND OF THE INVENTION

Description of the Prior Art

U.S. Pat. No. 4,340,592 describes nutrient compositions of dipeptides and tripeptides and the method of administering the compositions to mammals for dietary purposes. The important developments described in U.S. Pat. No. 4,340,592 provide a composition which can be employed to supplement nutritional deficiencies or to provide a complete nutritional composition, particularly for a comatose patient or a patient having metabolic or digestive interference. The introduction of large quantities of free amino acids into a mammal tends to establish hypertonicity and metabolic interference.

The expression "protein nutrients" herein includes free amino acids, organic acid amides of amino acids and oligopeptides.

The nutritional problems arising from using free amino acids could be avoided by employing an aqueous mixture containing oligopeptides, that is, dipeptides or tripeptides, of the essential amino acids and other amino acids wherein the N-terminal amino acid is a glycine residue. The glycine terminal amino acid residue achieves water solubility and achieves excellent absorption of the oligopeptides.

While the use of the described aqueous solution of glycine-terminated dipeptides and tripeptides achieves the objectives set forth, there are some improvements which are useful, particularly in providing a complete nutritional composition (1) There may be a tendency to develop excess glycine in the patient as a result of using glycine as the N-terminal amino acid residue in all of the oligopeptides. There is no evidence that excess glycine creates any medical problems.

(2) Free amino acids are limitedly soluble in water. Glycine terminated oligopeptides are highly soluble in water. However nutrient compositions containing glycine oligopeptides and/or free amino acids heretofore have been employed in concentrations of 20 weight percent peptide or less, usually less than 15 weight percent total protein content, i.e., the sum of the weight of oligopeptides and the weight of free amino acids. The use of such relatively low concentration aqueous nutrient compositions interferes with development of a complete nutrition system because of the water-intake limits for parenteral nutrition. There is an established limit for the amount of water which can be introduced parenterally into a patient. Approaching that water-intake limit will cause serious problems in medical patients having heart deficiencies or kidney deficiencies. Achieving and exceeding the water-intake limit may be fatal for such patients. Therefore such medical patients cannot be maintained parenterally for extended periods solely by prior art nutrient compositions. Such medical patients heretofore are effectively starving during those periods when they are unable to absorb nutrition except parenterally. It is possible to introduce maintenance-quantities of oligosaccharides, fats, minerals, trace elements and vitamins but it is not possible to introduce sufficient protein ingredients parenterally in the form of free amino acids.

STATEMENT OF THE PRESENT INVENTION

This continuation-in-part application recognizes that aqueous nutrient compositions can be employed in higher concentrations—up to about 40 weight percent total protein, i.e., the sum of the oligopeptides and the free amino acids—a much higher range than was heretofore believed to be possible.

The higher concentrations are achieved by combining free amino acids, as desired, with oligopeptides, as desired, to provide the proportions of total protein nutrients which are appropriate to the needs of the patient.

The potential glycine excess can be avoided by providing at least some of the oligopeptides as glycine-terminated oligopeptides and providing other oligopeptides which are terminated with alanine or arginine or lysine moieties. The concentration of the oligopeptides is from 0.2 to 30 parts by weight in the nutrient composition, preferably from 2 to 20 weight percent. The total protein content consisting of free amino acids and oligopeptides is from 2 to 40 weight percent. The high concentrations of protein ingredients permit reduced fluid loads for the patient.

Nutrient compositions having lower concentrations of protein ingredients are useful, particularly with certain essential amino acids such as tryptophan and tyrosine which are difficult to provide as parenteral nutrients.

According to the present invention, novel nutritional compositions are prepared which are aqueous solutions containing at least one oligopeptide of naturally-occurring amino acids consisting of a dipeptide or a tripeptide wherein the N-terminal amino acid residue is glycine residue, and at least one oligopeptide consisting of a dipeptide or a tripeptide wherein the N-terminal amino acid residue is selected from the class consisting of alanine, lysine and arginine.

The oligopeptide concentration is from 0.2 to 30 weight percent. For total parenteral nutrition, the preferred range is from 5 to 15 weight percent of the oligopeptide. The total protein nutrients in the compositions are from 2 to 40 weight percent. There are approximately 20 naturally-occurring amino acids, of which only eight are necessary (essential amino acids) in the human diet since the other can be synthesized by the body.

The oligopeptides of this invention are those containing moieties of the naturally-occurring amino acids, although the naturally-occurring amino acids may be synthesized composition. The phrase "naturally-occurring amino acids" comprehends those approximately 20 naturally-occurring amino acids regardless of whether the amino acids are derived from natural sources or are synthesized from non-natural starting materials.

The free amino acids are preferably those which can be supplied as aqueous solute and which have stability in storage. The oligopeptides preferably include amino acid moieties which are difficultly soluble in water and those which are unstable in the free amino acid state.

In order to develop a complete nutritional composition, the compositions also may contain other nutrient ingredients such as oligosaccharides, fats, minerals, trace elements, vitamins and free amino acids. The oligopeptides comprise from about 0.2 to 30 weight percent of the aqueous solution, preferably from 5 to 15 weight percent. The composition also may include free amino acids for the reasons already set forth. The composition is intended for oral, gastrointestinal or intravenous introduction into a patient.

DESCRIPTION OF THE PREFERRED EMBODIMENTS

The composition set forth in Table I has been prepared as a nutrient composition which has been effective to maintain a laboratory animal as a complete nutritional source for an extended period of time.

TABLE I

| Aqueous Nutrient Composition of Investigation 1 | |
|---|---|
| Dipeptide | Concentration (millimoles/liter) |
| Gly-L-Thr | 10.8 |
| Gly-L-Val | 16.3 |
| Gly-L-Met | 7.6 |
| Gly-L-Ile | 12.9 |
| Gly-L-Leu | 18.8 |
| Lys-L-Lys | 5.0 |
| Gly-L-Trp | 3.0 |
| Gly-L-His | 6.0 |
| Gly-L-Phe | 7.6 |
| Arg-L-Glu | 12.6 |
| Gly-L-Pro | 6.0 |
| Gly-L-Ala | 15.0 |
| Gly-L-Tyr | 6.0 |
| Gly-L-Gln | 30.0 |
| Ala-L-Ala | 39.3 |

The conventional abbreviations of Table I are:
Ala Alanine
Arg Arginine
Gln Glutamine
Glu Glutamic acid
Gly Glycine
His Histidine
Ile Isoleucine
Leu Leucine
Lys Lysine
Met Methionine
Phe Phenylalanine
Pro Proline
Thr Threonine
Trp Tryptophan
Tyr Tyrosine
Val Valine The Table 1 composition contains all of the essential amino acids and also includes some of the non-essential amino acids. It is well known that the essential amino acids include lysine, leucine, isoleucine, tryptophan, methionine, valine, phenylalanine, threonine. Non-essential amino acids include arginine, histidine, alanine, proline, glycine, glutamic acid, asparagine, aspartate, cysteine, glutamine, serine, taurine, hydroxyproline, citrulline, alpha-amino-n-butyric acid, cystathionine and ornithine.

It will be observed from Table I that most of the dipeptides in the nutrient composition have a glycine residue in the N-terminal position. However the Lys-L-Lys (Lysyl lysine), the Arg-L-Glu (Arginyl-glutamic acid) and the Ala-L-Ala (Alanyl-alanine) contain lysine, arginine and alanine, respectively as the N-terminal amino acid residue. The composition of Table I has been specially prepared to supply, as peptides, appropriate quantities of the essential amino acids and appropriate quantities of some important non-essential amino acids. By employing some dipeptides which are terminated with the lysine, alanine, arginine residues, the tendency for the patient to develop glycine excess is avoided. In a preferred nutrient composition, the dipeptide formulation of Table I is combined with life-maintenance quantities of oligosaccharides, fats, minerals, vitamins and free amino acids as an aqueous mixture which functions as a complete nutrient composition, particularly for a patient who is comatose or afflicted with gastro-intestinal problems resulting from illness, injury or surgery.

The nutrient compositions of this invention may be administered as described in the aforementioned U.S. Pat. No. 4,340,592, e.g., orally, intragastrointestinally and intravenously.

Nutrient compositions were prepared containing glycine terminated dipeptides as shown in Table 2.

TABLE 2

| Aqueous Nutrient Composition of Investigation 2 | |
|---|---|
| Dipeptide | Concentration (millimoles/liter) |
| Gly-L-Thr | 6.80 |
| Gly-L-Val | 10.37 |
| Gly-L-Met | 11.41 |
| Gly-L-Ile | 9.88 |
| Gly-L-Leu | 13.59 |
| Gly-L-Phe | 10.79 |
| Gly-L-Lys | 11.09 |
| Gly-L-His | 5.22 |
| Gly-L-Arg | 18.61 |
| Gly-L-Ala | 56.72 |
| Gly-L-Pro | 32.41 |
| Gly-L-Trp | 1.98 |

The Table 2 composition, which also contained fat, glucose, electrolytes, minerals, trace elements and vitamins, was administered parenterally as the sole nutrient for laboratory animals over an extended period of time. The laboratory animals did not exhibit any ill effects from the parenteral nutrition investigation when the dipeptide mixture of Table 2 was employed. At the end of the investigation, the glycine content of the laboratory animal plasma was 1336 (+/− 108) micromoles. The laboratory animals exhibited no ill effects associated with the elevated glycine content. The normal glycine content of the laboratory animal's plasma is about 371 to 626 micromoles.

The described laboratory animal investigation is reported in Gastroenterology, 1984; 86:1562–69 in an article entitled "Efficacy of a Synthetic Dipeptide Mixture as the Source of Amino Acids for Total Parenteral Nutrition in a Subhuman Primate (Baboon)—Plasma Concentration, Metabolic Clearance, and Urinary Excretion of a Series of Dipeptides" by Steinhardt, Paleos, Brandl, Fekl and Abidi.

Additional investigations were carried out with a peptide composition set forth in Table 3.

TABLE 3

| Aqueous Nutrient Composition of Investigation 3 Protein Nutrient Content 20 Weight Percent | | |
|---|---|---|
| | Concentration | |
| Substance | millimoles per liter | grams per liter |
| glycyl-L-isoleucine | 74.37 | 14.0 |
| L-isoleucine | 38.12 | 5.0 |
| glycyl-L-leucine | 85.00 | 16.0 |
| L-leucine | 41.93 | 5.5 |
| glycyl-L-valine | 137.76 | 24.0 |
| L-valine | 68.29 | 8.0 |
| glycyl-L-tyrosine | 31.46 | 7.5 |
| glycyl-L-glutamine | 44.29 | 9.0 |
| L-alanyl-L-glutamine | 20.72 | 4.5 |
| L-lysine-L-glutamate* | 37.50 | 11.0 |
| L-lysine | 41.04 | 6.0 |

TABLE 3-continued

Aqueous Nutrient Composition of Investigation 3
Protein Nutrient Content 20 Weight Percent

| Substance | Concentration millimoles per liter | grams per liter |
|---|---|---|
| L-ornithine-L-aspartate* | 28.27 | 7.5 |
| L-arginine | 52.81 | 9.2 |
| L-histidine | 59.29 | 9.2 |
| L-serine | 87.54 | 9.2 |
| L-threonine | 77.23 | 9.2 |
| L-alanine | 207.66 | 18.5 |
| L-proline | 79.91 | 9.2 |
| N-acetyl-L-cysteine* | 3.06 | 0.5 |
| L-methionine | 50.26 | 7.5 |
| L-phenylalanine | 33.29 | 5.5 |
| L-tryptophan | 19.59 | 4.0 |
| Total | | 200.00 |

*Note L-lysine-L-glutamate is a salt of a basic amino acid and an acidic amino acid
L-ornithine-L-aspartate is a salt of basic and acidic non-essential amino acids.
N-acetyl-L-cysteine is an example of an organic acid amide of an amino acid It will be observed that the composition of Table 3 includes several free amino acids, one organic acid amide of an amino acid and also includes glycine-terminated dipeptides and includes alanine-terminated dipeptides. The total glycine concentration in this composition was 14 weight percent—compared to approximately 50 weight percent glycine in the dipeptide composition of Table 2.

Laboratory animal investigations were carried out with the nutrient composition of Table 3. Effective nutrition was achieved with the laboratory animals over extended periods. The glycine content of the laboratory animal plasma after this investigation was 736. The laboratory animals exhibited no ill effects which might be associated with nutrition.

The urinary excretion of dipeptides during the investigation was less than 1 percent of the amount of infused peptides, which suggests conversion and utilization of the parenterally introduced peptides. The tests established firm evidence for efficacy and safety of a dipeptide mixture as described as the sole nitrogen source for parenteral nutrition in mammals.

A typical nutrient composition for parenteral nutrition having a higher concentration of protein solute than previously contemplated is set forth in Table 4.

TABLE 4

Aqueous Nutrient Composition of Investigation 4
Protein Nutrient Content 40 Weight Percent

| Substance | Concentration grams per liter | millimoles per liter |
|---|---|---|
| glycyl-L-isoleucine | 16.1 | 85.54 |
| glycyl-L-leucine | 21.9 | 116.08 |
| glycyl-L-valine | 18.3 | 104.90 |
| L-alanyl-L-tyrosine | 17.6 | 69.76 |
| glycyl-L-glutamine | 35.5 | 174.92 |
| L-glutamic acid | 33.0 | 224.56 |
| L-lysine | 18.0 | 123.06 |
| L-arginine | 37.4 | 214.70 |
| L-histidine | 9.4 | 60.26 |
| L-serine | 37.4 | 355.90 |
| L-threonine | 14.4 | 121.10 |
| L-alanine | 69.5 | 779.66 |
| L-proline | 37.4 | 324.86 |
| N-acetyl-L-cysteine | 0.8 | 4.90 |
| L-methionine | 14.4 | 96.68 |
| L-phenylalanine | 13.4 | 80.86 |
| L-tryptophan | 5.6 | 27.46 |
| Total | 400.0 | |

In Table 4 the nutrient composition includes 11 weight percent peptides including glycine-terminated peptides and one alanyl-terminated peptide (Alanyltyrosine). Cysteine is presented as an amide of an organic acid. The total protein content (peptides and free amino acids) is 40 weight percent. Such concentrated, soluble total protein compositions are not proposed in the prior art. The compositions of Table 4 contains all of the essential amino acids either as free amino acids or as moieties of an oligopeptide.

The invention also contemplates protein nutrient compositions hang smaller quantities of oligopeptides as set forth in Table 5.

TABLE 5

Aqueous Nutrient Composition of Investigation 5
Protein Nutrient Content 10 Weight Percent

| Substance | Concentration grams per liter | millimoles per liter |
|---|---|---|
| L-alanyl-L-tryptophan | 2.00 | 7.26 |
| glycyl-L-tyrosine | 3.00 | 12.59 |
| L-isoleucine | 7.00 | 53.35 |
| L-leucine | 8.00 | 60.96 |
| L-valine | 11.50 | 98.16 |
| L-lysine-L-glutamate* | 11.00 | 37.50 |
| L-ornithine-L-aspartate* | 3.50 | 13.20 |
| L-arginine | 4.30 | 24.69 |
| L-histidine | 4.30 | 27.72 |
| L-serine | 4.30 | 40.92 |
| L-threonine | 4.30 | 36.10 |
| L-alanine | 13.00 | 145.89 |
| L-proline | 4.30 | 37.35 |
| N-acetyl-L-cysteine* | 0.50 | 3.06 |
| L-methionine | 3.50 | 23.45 |
| L-phenylalanine | 2.50 | 15.14 |
| glycine | 13.00 | 173.12 |
| Total | 100.00 | |

*See Footnote Table 3.

The dipeptides comprise 0.5 weight percent of a nutrient composition by weight as glycine and alanine terminated peptides. Cysteine is included as an amide of an organic acid. Free amino acids comprise 9.5 weight percent of the nutrient composition. The composition of Table 5 is particularly useful in maintaining nutrition for growing children who have continuing needs for tyrosine and tryptophan.

We claim:

1. An aqueous nutrient composition comprising from 20 to 40 weight percent of oligopeptides selected from the class consisting of dipeptides and tripeptides of naturally-occurring amino acids wherein at least one said oligopeptide contains a glycine residue as the N-terminal amino acid residue; and at least one said oligopeptide contains as the N-terminal amino acid residue an amino acid residue selected from the class consisting of alanine, lysine and arginine.

2. The aqueous nutrient composition of claim 1 including alanyl tyrosine as one of the said oligopeptides.

3. The aqueous nutrient composition of claim 1 including arginyl glutamic acid as one of the said oligopeptides.

4. The aqueous nutrient composition of claim 1 including lysyl lysine as one of the said oligopeptides.

5. The aqueous nutrient composition of claim 1 including at least one free amino acid.

6. The aqueous nutrient composition of claim 1 containing all of the essential amino acids, either as free amino acids or as amino acid residues in the said oligopeptides.

7. An aqueous nutrient composition according to claim 1 wherein at least one of said oligopeptides contains an alanine residue as the N-terminal amino acid residue.

8. An aqueous nutrient composition according to claim 1 wherein at least one of said oligopeptides contains a lysine residue as the N-terminal amino acid residue.

9. An aqueous nutrient composition according to claim 1 wherein at least one of said oligopeptides contains an arginine residue as the N-terminal amino acid residue.

10. An aqueous nutrient composition of claim 7 including at least one free amino acid.

11. An aqueous nutrient composition of claim 8 including at least one free amino acid.

12. An aqueous nutrient composition of claim 9 including at least one free amino acid.

13. An aqueous nutrient composition comprising from 20 to 40 weight percent of protein nutrients including 0.2 to 30 weight percent or dipeptides of L-threonine, L-valine, L-methionine, L-isoleucine, L-leucine, L-lysine, L-tryptophan, L-histidine, L-phenylalanine, L-glutamic acid, L-proline, L-glutamine, L-alanine and L-tyrosine, and, as the N-terminal residue of at least one of said dipeptides, a glycine residue and, as the N-terminal residue of at least one of said dipeptides, at least one other amino acid residue selected from the class consisting of L-alanine, L-lysine and L-arginine.

14. An aqueous parenteral nutrient composition comprising 20 to 40 percent by weight of protein nutrients including free amino acids and oligopeptides consisting of dipeptides or tripeptides of naturally-occurring amino acids, where the said oligopeptides comprise 2 to 20 weight percent of the composition.

* * * * *